(12) United States Patent
Horiuchi et al.

(10) Patent No.: US 8,647,589 B2
(45) Date of Patent: Feb. 11, 2014

(54) FLOW CELL AND METHOD FOR MANUFACTURING THE SAME

(75) Inventors: Tsutomu Horiuchi, Atsugi (JP); Toru Miura, Atsugi (JP); Yuzuru Iwasaki, Atsugi (JP); Jyunichi Takahashi, Atsugi (JP); Katsuyoshi Hayashi, Atsugi (JP); Tsuneyuki Haga, Atsugi (JP); Michiko Seyama, Atsugi (JP); Serge Camou, Atsugi (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 0 days.

(21) Appl. No.: 13/554,380

(22) Filed: Jul. 20, 2012

(65) Prior Publication Data

US 2012/0288421 A1    Nov. 15, 2012

Related U.S. Application Data

(63) Continuation of application No. 12/303,943, filed as application No. PCT/JP2007/062737 on Jun. 26, 2007, now abandoned.

(30) Foreign Application Priority Data

Jun. 26, 2006 (JP) .................................. 2006-175681
Jun. 26, 2006 (JP) .................................. 2006-175683

(51) Int. Cl.
*B01L 3/00* (2006.01)

(52) U.S. Cl.
USPC ........... 422/420; 422/421; 422/422; 422/423; 422/424; 422/425; 422/426; 422/427; 422/428; 422/429; 422/502; 422/503; 422/507; 435/287.7; 435/287.8

(58) Field of Classification Search
USPC ................. 422/417, 420–421, 422–424, 426, 422/502–503, 507, 535, 513, 527, 534, 422/427–429; 435/287.7, 287.8
See application file for complete search history.

(56) References Cited

U.S. PATENT DOCUMENTS 3,960,488 A    6/1976  Giaever
3,960,491 A    6/1976  Giaever
(Continued)

FOREIGN PATENT DOCUMENTS

EP    0418765    3/1991
GB    2342443    4/2000
(Continued)

OTHER PUBLICATIONS

U.S. Appl. No. 12/303,943, Dec. 8, 2011, Office Action.
(Continued)

*Primary Examiner* — Brian R Gordon
(74) *Attorney, Agent, or Firm* — Workman Nydegger

(57) ABSTRACT

An object of the invention is to provide various flow cells and a method for manufacturing the same, in which formation of a groove on a substrate and formation of components such as an electrode, auxiliary parts such as a pump are not necessary. The inventive flow cells are capable of realize complicated chemical analysis or synthesis or the like. A channel of a porous member provided on a sample-incompatible substrate is formed; the porous member is composed of an air non-contact region having a network structure and an air contact region covering the air non-contact region and having a lower pore density than the air non-contact region; in which a capillary force to be generated within the porous member is a drive force for pumping a liquid.

14 Claims, 30 Drawing Sheets

(56) References Cited

U.S. PATENT DOCUMENTS

| | | | |
|---|---|---|---|
| 4,166,093 A | | 8/1979 | Smith-Lewis et al. |
| 4,587,102 A | | 5/1986 | Nagatomo et al. |
| 4,774,192 A | | 9/1988 | Terminiello et al. |
| 4,994,238 A | * | 2/1991 | Daffern et al. ............... 422/422 |
| 5,023,052 A | | 6/1991 | Nagatomo et al. |
| 5,198,335 A | | 3/1993 | Sekikawa et al. |
| 5,565,170 A | * | 10/1996 | Sakamoto ..................... 422/422 |
| 5,755,231 A | * | 5/1998 | Krantz et al. ................. 600/368 |
| 5,766,552 A | | 6/1998 | Doshi et al. |
| 5,772,961 A | | 6/1998 | Mico |
| 5,789,255 A | * | 8/1998 | Yu .................................. 436/95 |
| 5,821,073 A | | 10/1998 | Lee |
| 5,989,840 A | | 11/1999 | D'Angelo et al. |
| 6,140,136 A | * | 10/2000 | Lee ............................... 436/518 |
| 6,197,494 B1 | | 3/2001 | Oberhardt |
| 6,528,323 B1 | * | 3/2003 | Thayer et al. ................. 436/518 |
| 6,537,496 B1 | | 3/2003 | Knappe et al. |
| 6,780,651 B2 | * | 8/2004 | Douglas et al. ............... 436/518 |
| 6,986,869 B2 | * | 1/2006 | Tuohy et al. .................. 422/422 |
| 6,991,940 B2 | * | 1/2006 | Carroll et al. ................. 436/514 |
| 7,049,130 B2 | * | 5/2006 | Carroll et al. ............... 435/287.2 |
| 7,160,590 B2 | | 1/2007 | Vanhamel et al. |
| 7,449,146 B2 | | 11/2008 | Rakow et al. |
| 7,476,533 B2 | * | 1/2009 | Meathrel et al. ........... 435/287.2 |
| 7,560,288 B2 | * | 7/2009 | Carroll et al. ................. 436/518 |
| 7,575,915 B2 | | 8/2009 | Nadaoka et al. |
| 7,605,004 B2 | * | 10/2009 | Zhou ............................. 436/518 |
| 7,632,687 B2 | * | 12/2009 | Gokhan ........................ 436/518 |
| 7,709,272 B2 | * | 5/2010 | Fuks et al. .................... 436/514 |
| 7,851,209 B2 | * | 12/2010 | Wei et al. ................... 435/288.7 |
| 7,955,791 B2 | * | 6/2011 | Dinello et al. ..................... 435/4 |
| 8,067,246 B2 | * | 11/2011 | Marlborough et al. ....... 436/518 |
| 2003/0096424 A1 | * | 5/2003 | Mao et al. ..................... 436/169 |
| 2008/0145835 A1 | * | 6/2008 | Alajem et al. ..................... 435/4 |
| 2009/0208920 A1 | * | 8/2009 | Ohman et al. ..................... 435/2 |
| 2010/0099112 A1 | * | 4/2010 | Zhou et al. ..................... 435/7.1 |
| 2010/0233033 A1 | | 9/2010 | Horiuchi et al. |

FOREIGN PATENT DOCUMENTS

| | | |
|---|---|---|
| JP | 07-036017 | 2/1995 |
| JP | 07-508350 | 9/1995 |
| JP | 11-037922 | 2/1999 |
| JP | 2001-89134 | 4/2001 |
| JP | 2004-250290 | 9/2004 |
| WO | WO 93/23755 | 11/1993 |

OTHER PUBLICATIONS

U.S. Appl. No. 12/303,943, Apr. 25, 2012, Office Action.
Joo-Eun Kim et al., Functional Membrane-Implanted Lab-on-a-Chip for Analysis of Percent HDL Cholesterol, Analytical Chemistry, vol. 77, 2005, pp. 7901-7907.
PCT Notification of Transmittal of Translation of the International Preliminary Report on Patentability (Chapter 1 or Chapter II of the Patent Cooperation Treaty) of related Japanese Application No. PCT/JP2007/062737, dated Feb. 12, 2009 (5 pages).
Supplementary European Search Report dated Jan. 2, 2012.

* cited by examiner

FLOW CELL AND METHOD FOR MANUFACTURING THE SAME

CROSS-REFERENCE TO RELATED APPLICATIONS

This application is a continuation of U.S. patent application Ser. No. 12/303,943 filed on Dec. 8, 2008 and entitled "FLOW CELL AND METHOD FOR MANUFACTURING THE SAME," which is a U.S. national phase of Patent Cooperation Treaty application PCT/JP2007/062737 filed on Jun. 26, 2007, which claims priority to Japanese patent applications 2006-175681 and 2006-175683, both filed on Jun. 26, 2006, the entirety of each of the above identified patent applications are incorporated herein by reference.

BACKGROUND OF THE INVENTION

1. Technical Field

The present invention relates to a flow cell which is utilized in the fields of handling a trace amount of solution, such as micro-TAS, Lab-on-a-chip, micro-combinatorial chemistry, chemical IC, chemical sensor, biosensor, microanalysis, electrochemical analysis, chromatography, QCM measurement, SPR measurement, ATR measurement, etc. In more detail, the invention relates to a flow cell in which a porous member having a sample-compatible interior is disposed on a sample-incompatible substrate and which does not require means for pumping a liquid from the outside, such as a pump, etc. Also, the invention relates to a flow cell further having a top cover. The invention also relates to a method for manufacturing the above-described flow cell.

2. Background Art

In each of the foregoing fields, there may be a case where it is necessary to transfer a solution micro-sample. Also, there is a possibility that efficiency, sensitivity and treatment ability for obtaining a desired result in each of the fields tremendously increase due to such transfer. To achieve the transfer of a solution micro-sample, there are known ways utilizing, for example: transferring a sample by a pressure from the outside on the assumption that a fine channel formed on a substrate is used; transfer by static electricity; electrowetting; utilizing a change of volume or formation of air bubbles by heating; electroosmosis flow; and the like.

However, in order to transfer a solution micro-sample by such means, it has been necessary to form a fine groove on a substrate by utilizing micromachining technology and/or to arrange components such as an electrode, a heater, etc. Also, in forming a channel, bonding between substrates to each other has been necessary. Furthermore, in the case of transferring a sample by a pressure from the outside, not only auxiliary parts such as a pump, a conduit, etc. are necessary, but also a so-called dead volume increases, and therefore, there has been limits in miniaturization of a measurement system or the like for achieving a reduction in the amount of the sample.

On the other hand, as a method for analyzing a solution micro-sample, paper chromatography utilizing an infiltrating effect of an aqueous solution into filter paper has been known. As means for detecting a biological substance, which is simple and easy and inexpensive, the immunochromatography method has been developed and improved (see, for example, Patent Document 1). Also, a measurement chip in which filter paper is arranged in a plastic channel is disclosed as an analogous technology (see, for example, Non-Patent Document 1).

Patent Document 1: Japanese Patent Publication No. 07-36017;
Patent Document 2: Japanese Patent Laid-Open No. 2001-89134;
Patent Document 3: Japanese Patent Laid-Open No. 2004-250290;
Non-Patent Document 1: J-E. Kim, et al, Anal. Chem., 2005, 77, 7901-7907.

DISCLOSURE OF THE INVENTION

Problems that the Invention is to Solve

In such a measurement chip in which processed filter paper is arranged in a channel made of plastic, etc., in the case where the filter paper comes into contact with the plastic, etc., there is a possibility that a solution will flow into the contact portion, and that the solution is not transferred by flowing through the inside of the filter paper. Also, in processing filter paper, microfabrication has reached the limits. In light of the above, from the viewpoints of the problem caused due to the arrangement of filter paper and the limits regarding the above-described microfabrication, the shape and function of the channel are limited, and it is difficult to freely handle the solution in the above-described measurement chip. Also, the measurement chip obtained by processing and arrangement of filter paper is poor in adhesiveness between the filter paper and the substrate so that it cannot be utilized for SPR (surface plasmon resonance) measurement. Therefore, the method utilizing filter paper was not necessarily suitable for performing complicated chemical analysis or synthesis or the like.

As described above, the formation of a groove by micromachining and the formation of components such as an electrode, etc. requires massive investment in plant and equipment, and manufacturing costs substantially increase. Therefore, such processing makes it difficult to put articles requiring such micromachining to practical use in the field, assuming one-time use in medical or civilian applications. Also, in the case where external components necessary for transferring a solution micro-sample, such as a pump, a power source, etc., are required, the size and weight as a measurement system is increased. Therefore, in the case of moving the measurement system into a desired place and simply performing the measurement (so-called on-site measurement), it was difficult to apply such a system in view of costs. Furthermore, it is important to realize the configuration of transferring a solution micro-sample on a substrate simply and easily at low costs. In addition, it is also desirable to freely handle the solution sample, thereby achieving complicated chemical analysis or synthesis or the like.

In light of the above, there is a demand for a flow cell which does not require the formation of a groove and components such as an electrode on a substrate by a micromachining technology, does not require auxiliary parts such as a pump, etc. and can achieve complicated chemical analysis or synthesis or the like by freely handling a solution sample.

Accordingly, an object of the invention is to provide various flow cells which do not require the formation of a groove and components such as an electrode, etc. on a substrate, do not require auxiliary parts such as a pump, etc. and are able to realize complicated chemical analysis or synthesis or the like. In particular, a further object of the invention is to provide a flow cell to be used for SPR measurement, which has a structure in which a molecular recognition material can be three-dimensionally fixed in a region where an evanescent wave exists. Also, another object of the invention is to provide a method for manufacturing such a flow cell.

Means for Solving the Problems

The flow cell of the invention comprises a sample-incompatible substrate and a channel of a porous member provided on the sample-incompatible substrate. The porous member includes an air non-contact region having a network structure and an air contact region covering the air non-contact region and having a lower pore density than the air non-contact region. A capillary force generated within the porous member is a drive force for pumping a liquid. Here, the air non-contact region may have higher sample compatibility than the air contact region. The porous member can be formed of cellulose. Also, the porous member may further contain fine particles.

In a flow cell of a modified embodiment of the invention, at least a part of the air contact region of the porous member may be peeled. Alternatively, at least a part of the porous member may communicate with a sample-compatible region formed on the surface of the sample-incompatible substrate and acting as a drain.

A flow cell of a further modified embodiment of the invention may further comprise a second sample-incompatible substrate disposed on the porous member via a fine gap. Here, it is desirable that a width of the fine gap falls within the range of from 10 to 100 μm. Furthermore, the second sample-incompatible substrate may include a level difference section which is opposed to the porous member.

The above-described flow cell may be configured so as to have a structure suitable for the SPR measurement by making the sample-incompatible substrate transparent and further providing a metal thin film between the sample-incompatible substrate and the porous member. If so, it is desirable that the porous member has an average refractive index in a hydrous state lower than a refractive index of a prism to be used for the SPR measurement.

The method for manufacturing a flow cell of the invention comprises the steps of:

(a) preparing a coating solution having a porous material dissolved in a solvent mixture of a good solvent with high volatility and a poor solvent with low volatility;

(b) applying the coating solution onto a sample-incompatible substrate; and (c) evaporating the solvent mixture, thereby forming a porous member composed of an air non-contact region having a network structure and an air contact region covering the air non-contact region and having a lower pore density than the air non-contact region.

Here, the porous material may be cellulose. Also, the step (b) may be carried out by (1) drawing by a dispensing device or (2) placing a screen mask or a sealing member having a desired shape on the sample-incompatible substrate and applying the coating solution in an opening of the screen mask or sealing member. Alternatively, a porous member comprising a plurality of portions may be formed by preparing a first coating solution containing a fine particle and a second coating solution not containing a fine particle in the step (a) and separately applying the first and second coating solutions at the same time in the step (b).

A modified embodiment of the method for manufacturing a flow cell of the invention may further comprise (d) regulating a sample transfer rate in the porous member. The step (d) can be carried out by application of a pressure by a die, coating of a sealing material, exposure to a solvent vapor or dropping of a surfactant.

Another modified embodiment of the method for manufacturing a flow cell of the invention may further comprise (e) peeling a part of the air contact region of the porous member. The step (e) can be carried out by peeling by an adhesive tape or reactive ion etching.

A further modified embodiment of the method for manufacturing a flow cell of the invention may comprise (f) disposing a second sample-incompatible substrate on the porous member via a fine gap. Here, it is desirable that a width of the fine gap falls within the range of from 10 to 100 μm. Furthermore, the second sample-incompatible substrate may include a level difference section which is opposed to the porous member.

Advantages of the Invention

By adopting the above-described configurations, the flow cell of the invention provides to the following advantages.

(1) Since a capillary force of the porous member is used as a drive force for pumping a liquid, the formation of a groove on the substrate by a micromachining technology and the formation of components such as an electrode, etc. are not needed, and auxiliary parts such as a pump, etc. are not required.

(2) By properly setting up the shape of the porous member, it is possible to freely handle the solution sample, thereby realizing complicated chemical analysis (for example, SPR measurement, etc.) or synthesis or the like.

DETAILED DESCRIPTION OF THE PREFERRED EMBODIMENTS

Explanation of Reference Numerals

Figure 1A:
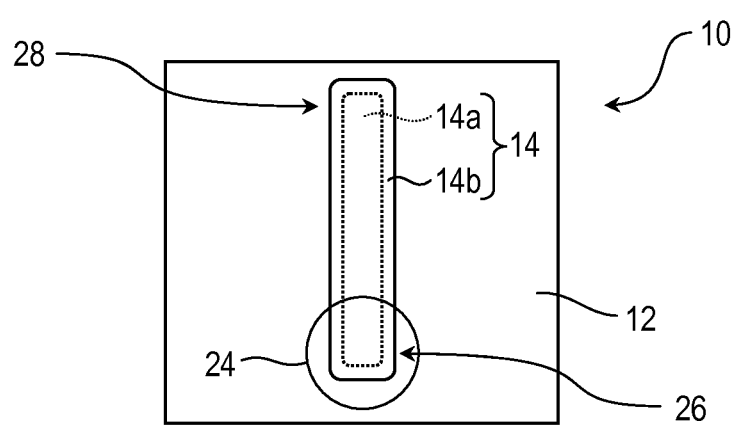
FIG. 1A is a plan view of a flow cell of Embodiment 1 of the invention.

10: Flow cell
12: Sample-incompatible substrate
14: Porous member
14a: Air non-contact region
14b: Air contact region
18: Porous material solution
20: Syringe
22: Linear pattern
24: Sample dropping region

BEST MODES FOR CARRYING OUT THE INVENTION

Hereinafter, the flow cell and method for manufacturing the same according to the invention are described in detail with reference to the accompanying drawings.

Embodiment 1

Figure 1B:
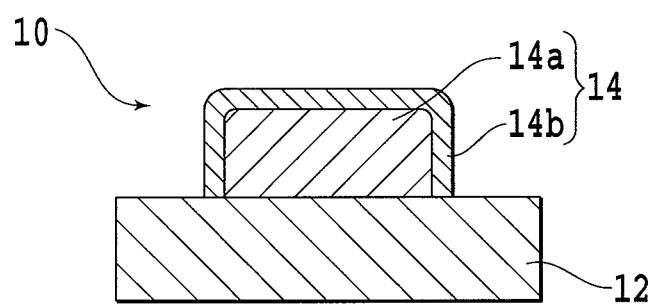
FIG. 1B is a cross-sectional view of a flow cell of Embodiment 1 of the invention.
Figure 1C:
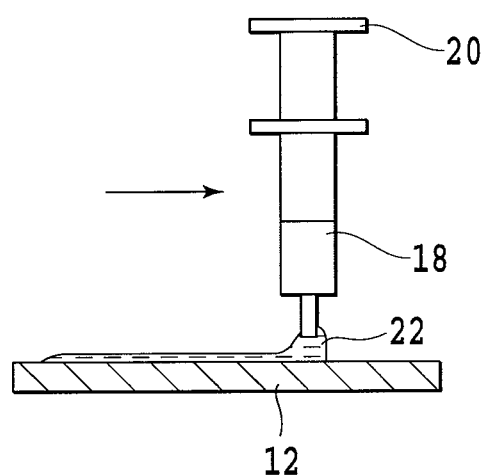
FIG. 1C is a view showing an example of a method for producing a flow cell of Embodiment 1 of the invention.

FIG. 1A is a top view of a flow cell of this embodiment; FIG. 1B is a cross-sectional view of a flow cell of this embodiment; and FIG. 1C is a view for explaining a method for manufacturing a flow cell of the invention. As shown in FIGS. 1A and 1B, a flow cell 10 of the invention is composed of a sample-incompatible substrate 12 and a porous member 14 provided on the substrate 12. The porous member 14 is composed of an air non-contact region 14a and an air contact region 14b covering the air non-contact region 14a and having a lower pore density than the air non-contact region 14a. The air non-contact region 14a is a region having a network structure and having higher sample compatibility. The air contact region 14b is a region having sample incompatibility as compared with the air non-contact region 14a. Both of these regions 14a and 14b form a channel having a network structure. The terms "pore density" as referred to in the invention mean a proportion of pores existing in a prescribed region within the network structure, and, for example, the state where the pore density is high refers to a state where a proportion of a network element constituting the network structure is low.

With such a configuration, the flow cell 10 uses a capillary force generated in the porous member 14 as a drive force for pumping a liquid. The drive principle thereof is as follows. That is, in dropping a solution micro-sample on one end 26 of the porous member 14 of the flow cell 10, the sample remains as a droplet on the spot due to a difference between a surface tension of the sample against the sample-incompatible substrate 12 and against the sample-incompatible air contact region 14b. Accordingly, the sample passes through the air contact region 14b of the porous member 14 and penetrates into the inside thereof (i.e., into the air non-contact region 14a) without being spread onto the sample-incompatible substrate 12. Subsequently, the sample which has passed through the air contact region 14b and reached the air non-contact region 14a gradually diffuses and penetrates due to a capillary phenomenon by the network structure of the sample-compatible air non-contact region 14a. Here, since a number of fine pores which are uniformly formed in the air contact region 14b act as a gas vent, after the sample has reached the air non-contact region 14a, an internal pressure in the porous member 14 does not increase. Accordingly, the sample is able to reach the opposite side 28 of the porous member 14 without any obstacle. As such, the air non-contact region 14a forms a channel through which the sample laterally flows from one end 26 of the air non-contact region 14a to the opposite end 28' when fine pores are present in a side portion of the air contact region 14b, the substrate 12 is sample-incompatible, and therefore, the sample does not leak out onto the sample-incompatible substrate 12.

The above-described elements are described respectively. As the sample-incompatible substrate 12, glasses, plastics, metals, semiconductors, etc.; substrates obtained by subjecting the surface of the above-described materials to a sample incompatibilizing treatment by means of chemical modification, etc.; and the like can be used. In the case of using an aqueous sample, the sample-incompatible substrate 12 is hydrophobic; and in the case of using a non-aqueous sample, the sample-incompatible substrate 12 is hydrophilic. Also, from the viewpoint of manufacture, it is preferable to use a substrate that has a high degree of flatness and is solvent resistant.

As the porous member 14 having a sample-compatible interior region, members such as cellulose, porous glass, a zeolite, etc. can be used; and from the viewpoint of manufacturing costs, it is especially preferable to use cellulose. As the cellulose, nitrocellulose, cellulose acetate, methyl cellulose and the like are useful; and taking into consideration the adhesiveness to the sample-incompatible substrate 12 and the pore density, it is necessary to choose a material from which a desired structure is obtainable. Here, the porous member 14 is composed of the air non-contact region 14a and the air contact region 14b. Also, it is desirable that the air non-contact region 14a has higher sample compatibility than the air contact region 14b. The "sample compatibility" and "sample incompatibility" of both regions 14a and 14b as referred to in the invention mean a degree of relative sample compatibility (or sample incompatibility) of both regions 14a and 14b. That is, in the porous member 14 using a cellulose, a hydrophilic (110) plane preferentially exists in the air non-contact region 14a, whereas a hydrophobic (110) plane preferentially exists in the air contact region 14b.

Next, the method for manufacturing a flow cell of this embodiment is described. In manufacturing such a flow cell 10, for example, a thin film of gold is first formed on a glass material and subsequently subjected to a treatment which makes the thin film incompatible with the sample, thereby preparing the sample-incompatible substrate 12. Then, a mixed solvent obtained by mixing a good solvent having a high volatility (for example, ketones) and a poor solvent with lower volatility (for example, alcohols or water) in a prescribed proportion is added to the cellulose to prepare a porous material solution 18. Subsequently, this solution 18 is filled in a dispenser such as a syringe 20 as shown in FIG. 1C, etc., and the syringe 20 is moved in the direction of the arrow while discharging the solution 18, thereby drawing a linear pattern 22. Also, in the case of using porous glass, the steps of applying and baking a mixture of glass material particles and a binder are repeated. The porous member 14 can be formed by reducing the glass material particles by step by step repetition. Also, in the case of using a zeolite, the porous member 14 can be formed; for example, by forming a film on the sample-incompatible substrate 12 by employing an electrophoretic deposition method, and subsequently densifying the film by a hydrothermal treatment, etc. (see Patent Document 2). Alternatively, the zeolite porous member 14 can be formed by employing a gentle film forming method in a dilute solution into which raw material components are continuously fed (see Patent Document 3).

The linear pattern 22 formed on the sample-incompatible substrate 12 is allowed to stand in air at room temperature, thereby evaporating the solvent components in the pattern 22. At the time of this evaporation step, the linear pattern 22 which was transparent at the beginning gradually becomes cloudy, whereby the porous member 14 is formed to obtain the flow cell 10. The air non-contact region 14a and the air contact region 14b have a different pore density due to a difference of evaporation behavior between the two solvent components at the time of the evaporation step. Here, it is preferable that the solvent components are evaporated uniformly (for example, isotropically) over the entire linear pattern 22 such that a large local difference is not generated in the thickness of the air contact region 14b.

The principle at which the regions having a different pore density are formed due to a difference of this evaporation behavior is as follows. In an initial stage of the evaporation, the good solvent having a high evaporation rate mainly evaporates, and the poor solvent having a low evaporation rate remains. Thus, a network structure is formed inside of the linear pattern 22. On the other hand, in a portion where the linear pattern 22 is in contact with air, the good solvent which evaporates from the inside passes there through, and therefore, the cellulose is present in a dissolved state. Here, in the portion in contact with air, the poor solvent also evaporates, and therefore, a proportion of the poor solvent is decreased. After completion of the evaporation of the good solvent from the inside, the evaporation also occurs in the portion in contact with air. However, since the proportion of the poor solvent has been decreased, the network becomes dense. In this way, the air contact region 14b having a low pore density is formed. In a final stage of the evaporation, the poor solvent evaporates and is replaced with air. The porous member 14 gets a cloudy appearance due to scattering of light because of a large difference in refractive index between air and the network element.

Example 1

The present inventors actually prepared the flow cell 10 as shown in FIG. 1 and examined a transfer rate of a solution micro-sample. A porous member 14 having a length of 1 cm and a width of 1 mm was formed on the sample-incompatible substrate 12, and 5 μL of a sample aqueous solution containing a dye (Red No. 102 (manufactured by Kyoritsu Foods Co., Inc.) was dropped onto a region 24 of one end 26 of the porous member 14 as shown in FIG. 1A. Though the aqueous solution remained as a droplet at the beginning, it immediately penetrated into the porous member 14, and 4 minutes after dropping, it reached the laterally opposite end 26 of the porous member 14.

In this sample solution dropping, leakage of the sample aqueous solution from the side face of the porous member 14 to the sample-incompatible substrate 12 was not observed at all, until the sample aqueous solution reached the opposite end 26. Thus, a flow cell was prepared which had a transfer rate of about 2.5 mm/min, which does not require a pump.

Embodiment 2

Figure 2A:
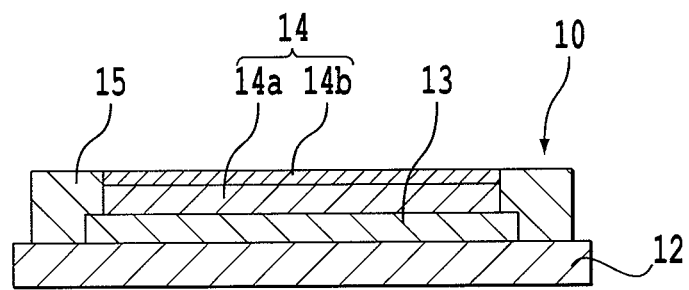
FIG. 2A is a cross-sectional view of a flow cell of Embodiment 2 of the invention.
Figure 2B:
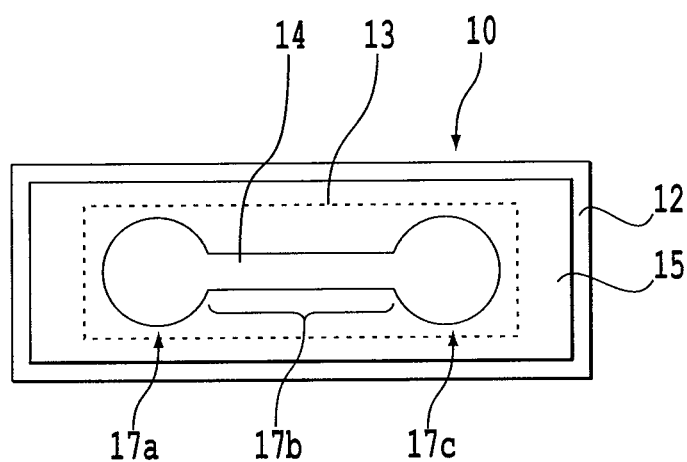
FIG. 2B is a top view of a flow cell of Embodiment 2 of the invention.

This embodiment relates to a flow cell which is suitable for the surface plasmon resonance (SPR) measurement. FIG. 2A shows a cross-sectional view of a configuration example of a flow cell of this embodiment; and FIG. 2B shows a top view of a configuration example of a flow cell of this embodiment. The flow cell of this embodiment is analogous to that of Embodiment 1, except for the points that the sample-incompatible substrate 12 is transparent; and that a metal thin film 13 is provided between the sample-incompatible substrate 12 and the porous member 14.

In the present invention, the "transparent" sample-incompatible substrate 12 means a substrate which is transparent at wavelengths of excitation light (incident light) and reflected light to be used for the measurement. The sample-incompatible substrate 12 of this embodiment can be formed by using a transparent material (for example, glass, etc.) among the materials as described in Embodiment 1.

The metal thin film 13 is a metal-made thin film for exciting a surface plasmon existing on the metal surface. The metal thin film 13 can be prepared by using a metal such as gold, silver, copper, etc. Also, for the purpose of efficiently coupling an evanescent wave in the porous member 14 with the surface plasmon, it is desirable that the metal thin film 13 has a thickness of from about 40 to 50 nm. The metal thin film 13 can be formed by employing any method known in the art, such as vapor deposition, sputtering, ion plating, laser ablation, etc.

The porous member 14 can be formed by using the materials and method as described in Embodiment 1. In this embodiment, the porous member 14 is also comprises the air non-contact region 14a and the air contact region 14b covering the air non-contact region 14a and having a lower pore density than the air non-contact region 14a. In this embodiment, it is desirable that the porous member 14 is prepared by using a cellulose. It is desirable that the porous member 14 of this embodiment has an average refractive index in a hydrous state lower than a refractive index of a prism to be used for the surface plasmon resonance measurement. By having a refractive index falling within such a range, there is obtained an advantage that the excitation conditions of an evanescent wave are satisfied. In the present invention, the "average refractive index" means a refractive index of a film having a fine structure (for example, fine pores, etc.) to be measured on the assumption that the film has a uniform structure. Also, in the present invention, the "hydrous state" means a state that a porous membrane is impregnated with pure water and reaches equilibrium.

Prior to the formation of the porous member 14, a sealing member 15 may be disposed on the metal thin film 13, thereby delimiting the formation position and shape of the porous member 14 (see FIGS. 2A and 2B). A coating method such as a spin coating method, etc. can be employed for the formation of the porous member 14 by using the sealing member 15. As the material for forming the sealing member 15, materials capable of being subjected to patterning are useful. Examples of such a material include polymer materials such as photoresists, etc.; inorganic oxides or nitrides such as $SiO_2$, $Al_2O_3$, $Si_3N_4$, AlN, etc.; metals; semiconductors; and the like. The formation of the sealing member 15 can be carried out by employing any method known in the art.

The fine pores of the porous member thus formed provide a suitable structure for three-dimensionally fixing a molecular recognition material such as antibodies, enzymes, nucleic acids (including oligonucleotides, polynucleotides, etc.), etc. in a region where an evanescent wave exists. Such a molecular recognition material may be physically adsorbed on the surface of a cellulose derivative, or may be chemically bonded onto the surface of a cellulose through a functional group which is reactive with the functional group (for example, a hydroxyl group, etc.) on the surface of the cellulose.

By changing a blending ratio of the cellulose-containing coating solution or the like, it is possible to change the size of the fine pores within the porous member 14 (especially, the air non-contact region 14a) from not more than about 1 μm to about 10 μm. Also, in addition to the blending ratio of the cellulose-containing coating solution, by changing the coating conditions or evaporation conditions of the solvent or the like, it is possible to obtain a porous member 14 having a thickness ranging from about 500 nm to about 10 μm. Accordingly, it is possible to obtain the porous member 14 which is optimal for fixing various molecular recognition materials, and to obtain a flow cell which is useful for the measurement of various kinds of molecules which are objective to the measurement.

Also, flow cells of other embodiments described in the present specification can be formed into a flow cell which is suitable for the SPR measurement, by using a transparent sample-incompatible substrate and further providing a metal thin membrane between the sample-incompatible substrate and the porous member.

Example 2

A gold thin film 13 having a thickness of 50 nm was formed on the glass substrate 12 by a vacuum vapor deposition method. Subsequently, the sealing member 15 covering the gold thin film 13 and having an opening of a desired shape was formed by using a photoresist. Next, the porous member 14 configured with a sample introduction section 17a, a channel 17b (1 cm in length×2 mm in width×1 μm in thickness) and a sample discharge section 17c was formed in the opening, by a spin coating method in which a cellulose acetate solution in an acetone/ethanol mixed solvent is dropped, thereby obtaining a sensor substrate as shown in FIGS. 2A and 2B.

A liquid sample such as pure water, a phosphoric acid buffer solution (PBS), a mixed solution of PBS and an antibody or antigen, etc. was dropped onto the sample introduction section 17a of the obtained sensor substrate. Then, the liquid sample was smoothly moved to the sample discharge section 17c through the channel 17b. Also, the porous member 14 of the obtained sensor substrate had an average refractive index in a hydrous state which is suitable for the SPR measurement using a prism having a refractive index of 1.51.

Example 3

Figure 3:
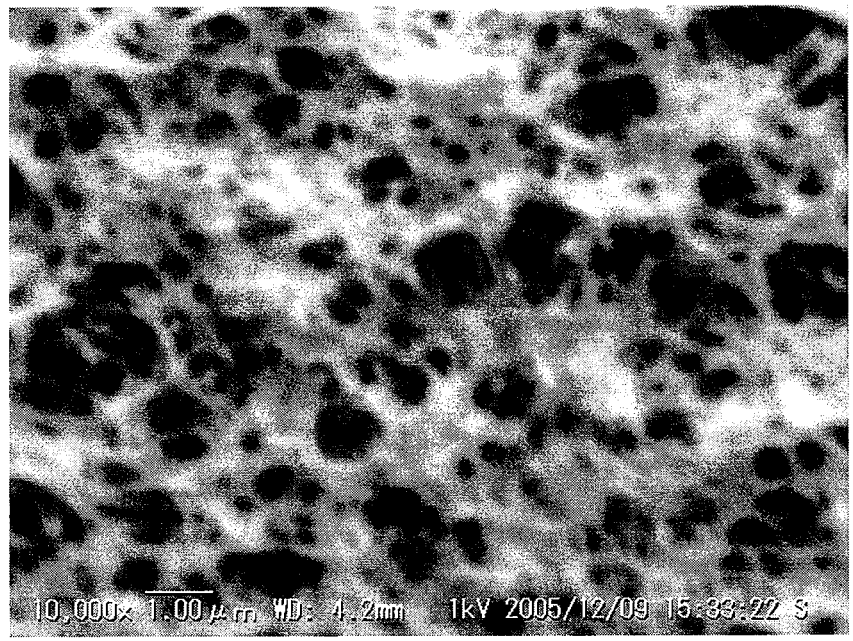
FIG. 3 is a view showing an electron microscopic photograph of a high-density porous membrane obtained in Example 3.

A porous member was formed on a glass substrate having a 50 nm-thick gold thin film formed thereon by employing a spin coating method in which a nitrocellulose solution (nitrocellulose content: about 9.2% by weight) in an acetone/isopropanol (IPA) mixed solvent was dropped. As a result, a porous member as shown in FIG. 3 was obtained. The porous membrane has a large number of fine pores per unit volume and is capable of providing a larger number of fixing sites for a molecular recognition material.

Figure 4:
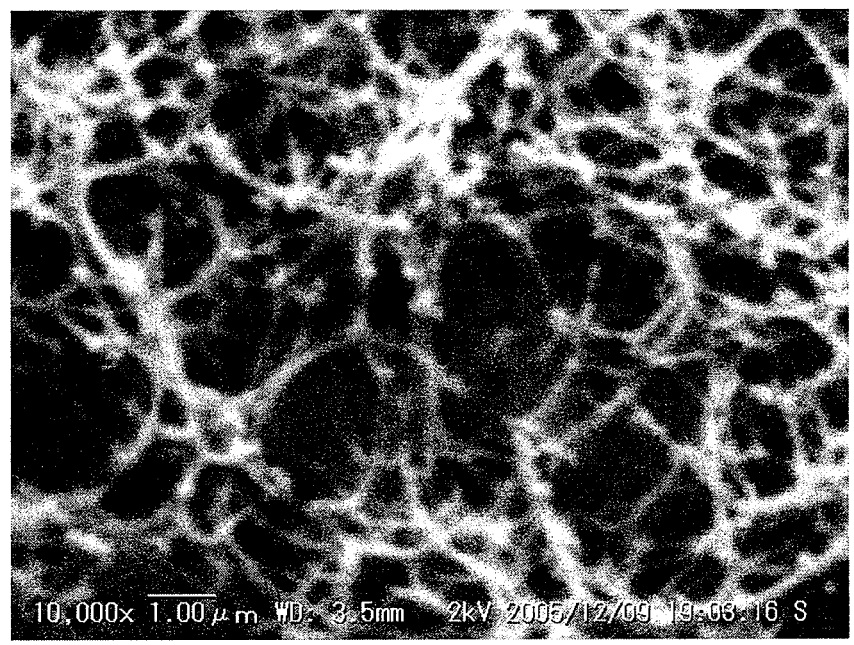
FIG. 4 is a view showing an electron microscopic photograph of a low-density porous membrane obtained in Example 3.

On the other hand, a porous member was formed by a spin coating method under the same condition, except for using a separate nitrocellulose solution (nitrocellulose content: about 7.8% by weight) in an acetone/IPA mixed solvent. As a result, a porous member as shown in FIG. 4 was obtained. The porous membrane has a small number of fine pores per unit volume but has a larger fine pore size, and thereby, is suitable for fixing of a molecular recognition material of a larger size.

In light of the above, it has become clear that a porous member having a desired suitability can be prepared for different purposes by changing blending of a solution of a cellulose derivative to be used.

Example 4

A porous member was formed on a glass substrate having a 50 nm-thick gold thin film formed thereon by a spin coating method in which a nitrocellulose solution in an acetone/isopropanol mixed solvent was dropped under conditions at 1,000 rpm for 10 seconds and subsequently at 4,000 rpm for 60 seconds. The obtained porous member had a thickness of 1.3 μm.

A porous membrane was also formed by using the same substrate and solution, except for changing the conditions of the spin coating method to that at 1,000 rpm for 10 seconds and subsequently at 8,000 rpm for 60 seconds. The obtained porous member had a thickness of 500 nm.

In light of the above, it has become clear that a porous member having a desired thickness can be formed by changing the condition of the spin coating method to be employed.

Embodiment 3

Figure 5A:
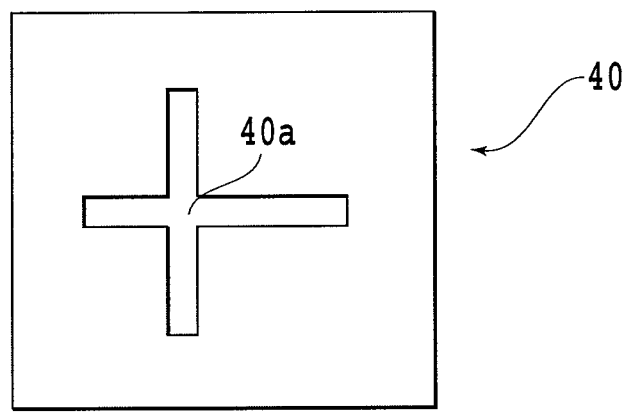
FIG. 5A is a plan view showing a flow cell after patterning of Embodiment 3 of the invention.
Figure 5B:
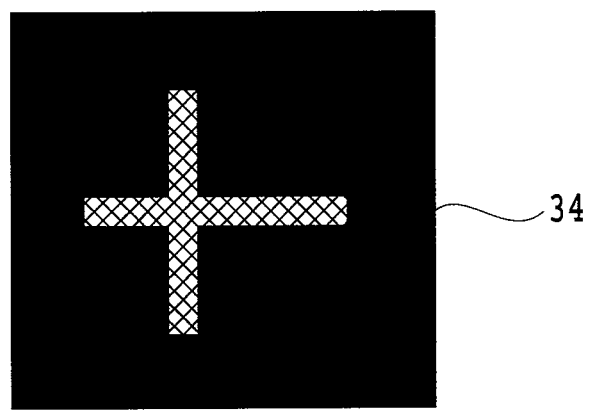
FIG. 5B is a plan view showing a screen mask to be used for patterning in a method for manufacturing a flow cell of Embodiment 3 of the invention.
Figure 5C:
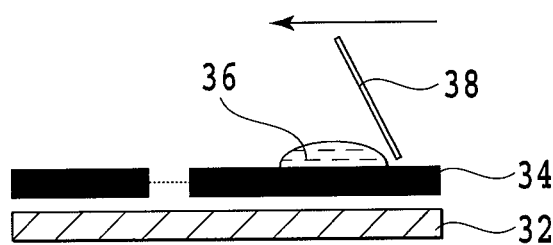
FIG. 5C is a view showing application of a membrane material by a squeeze in a laminated state of a sample-incompatible substrate and a screen mask at the time of patterning in a method for manufacturing a flow cell of Embodiment 3 of the invention.

This embodiment relates to a modification of the method for manufacturing a flow cell of the invention by the use of screen printing. FIG. 5A is a plan view showing a flow cell after patterning; FIG. 5B is a plan view showing a screen mask to be used for patterning; and FIG. 5C is a side view showing an application mode of a membrane material in a laminated state of a sample-incompatible substrate and a screen mask at the time of patterning by a squeeze. The slant lines in FIG. 5B and the dotted lines in FIG. 5C show the mesh of the screen.

In the pattern drawing as in Embodiment 1 (FIG. 1C), the evaporation of the solvent from the pattern starts in order from a portion which has been drawn, during drawing to be continuously carried out. In such a situation, when drawing a relatively complicated pattern, for example, a merged channel or a branched channel, the same place and the vicinity thereof must be again applied for drawing the vicinity of the merged section or branched section. Therefore, continuous drawing cannot be achieved over the whole of a desired pattern, to form a porous member whose network structure is discontinuous. A flow cell including a porous member having a discontinuous network structure as described above is not suitable for the use as a prescribed channel, since it is difficult to estimate a transfer rate of the liquid sample.

In order to overcome such a defect, according to the method of this embodiment, as shown in FIG. 5C, a screen mask 34 is arranged on a sample-incompatible substrate 32, then a solution 36 containing a material of a porous member is disposed on the screen mask 34, and a squeegee 38 is, for example, moved in the direction of the arrow, thereby applying a pattern. According to such a method, as shown in, for example, FIG. 5A, a flow cell 40 having a merged channel 40a comprising a porous member having a continuous network structure can be obtained.

In this embodiment, the screen mask 34 can be prepared by transferring a channel pattern on Mesh #120 or Mesh #230 (manufactured by Taiyo-Seiki Co., Ltd.). Mesh #120 is suitable for preparing a porous member (channel) having a line width of about 1 mm by using a solution with high viscosity in which a cellulose is dissolved in a high concentration. Also, Mesh #230 is suitable for preparing a porous member (channel) having a line width of about 0.5 mm by using a solution with low viscosity in which a cellulose is dissolved in a low concentration. Furthermore, the transfer rate of the squeeze 38 is not particularly limited, and any rate can be adopted so far as not only the network structure of the porous member can be made continuous, but also the network structure can be made uniform.

According to the manufacturing method of this embodiment, even in the case of applying a complicated pattern, for example, a merged channel or a branched channel, a desired pattern can be continuously applied. Accordingly, evaporation of the solvent simultaneously occurs within a desired pattern shape. Therefore, it is possible to obtain a flow cell including a continuous porous member as the whole of a desired pattern, in which a prescribed channel is formed at high precision.

Embodiment 4

Figure 6A:
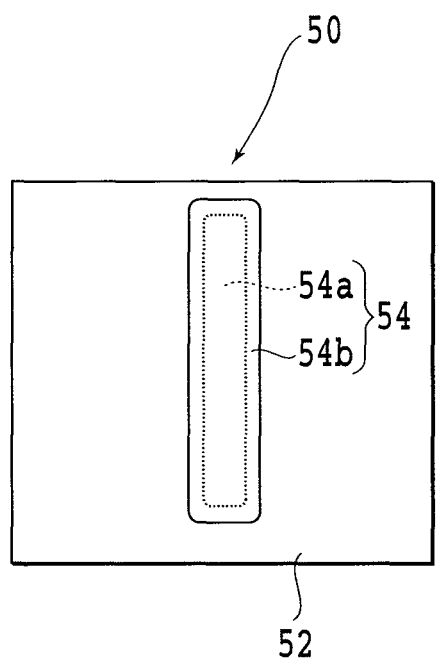
FIG. 6A is a plan view of a flow cell of Embodiment 4 of the invention.

FIG. 6A is a plan view showing an example of a modification of the flow cell of Embodiment 1. In this embodiment, fine particles were mixed in a solution of a cellulose dissolved in a mixed solvent obtained by mixing a good solvent and a poor solvent in a prescribed proportion. The resulting suspension was filled in a dispenser (for example, the syringe as shown in FIG. 1C, etc.). Subsequently, a linear pattern was drawn and then dried in the same manner as in Embodiment 1. In this embodiment, the porous member may also be formed by the spin coating method accompanied by the sealing member as shown in Embodiment 2 or the screen printing method as shown in Embodiment 3.

In this embodiment, as the fine particles, inorganic materials such as glass, a zeolite, etc.; plastic materials having a uniform particle size; and the like are useful. In this embodiment, from the viewpoints of absorbing ability of the solution sample and adhesiveness to the cellulose network structure, as the inorganic porous powder, it is preferable to use an inorganic porous powder 58 having a number of fine pores as the fine particles. Examples of the inorganic porous powder 58 which can be used in this embodiment include Vycor glass, a zeolite, mesoporous silica, etc.

Figure 6B:
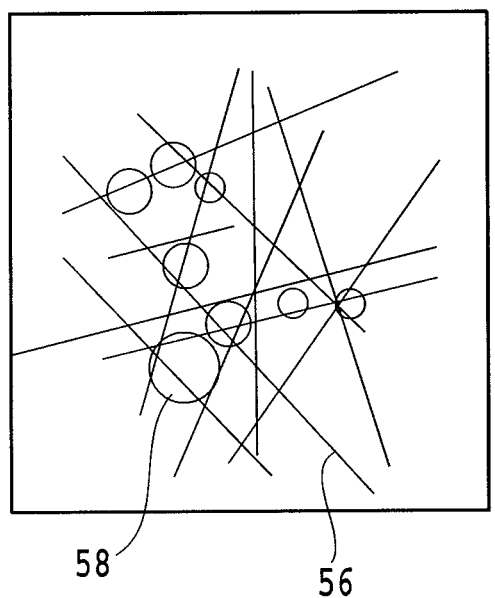
FIG. 6B is a diagrammatic view showing a structure of a porous member of a flow cell of Embodiment 4 of the invention.

In a flow cell 50 formed by such a method, a porous member 54 is formed on a sample-incompatible substrate 52 as shown in FIG. 6A. This porous member 54 is formed of an air non-contact region 54a having a network structure and an air contact region 54b covering the air non-contact region 54a as explained in Embodiment 1. Also, in this embodiment, as shown in FIG. 6B, the porous member 54 is composed of a network element (skeleton) 56 configuring the network structure and the inorganic porous fine powder 58, and as shown in the same portion, the fine powder 58 is irregularly dispersed in the network element 56.

Example 5

The present inventors actually prepared the flow cell as shown in FIG. 6A and examined a transfer rate of a solution microsample. The porous member 54 having a length of 1 cm and a width of 1 mm and having the inorganic porous fine powder 58 incorporated therein was formed on the sample-incompatible substrate 52. Next, 5 μL of an aqueous solution containing a dye (Red No. 102 (manufactured by Kyoritsu Foods Co., Inc.) was dropped on one end of the porous member 54. Though the aqueous solution remained as a droplet at the beginning, it thereafter penetrated into the porous member 54, and after 30 seconds, it reached an end of the opposite side.

At that time, a transfer rate of the solution microsample was 20 ram/min, a value which was larger than the transfer rate of the flow cell of Example 1. This increase of the transfer rate of the sample was caused by the fact that the porous member 54 had a structure in which the inorganic porous fine powder 58 was incorporated into the network element 56 composed of a cellulose, and as a result, its water absorbing ability was enhanced as compared with the porous member of Embodiment 1. In Embodiment 3, a flow cell is provided which has a transfer rate of about 20 mm/min and not requiring a pump.

Embodiment 5

Figure 7A:
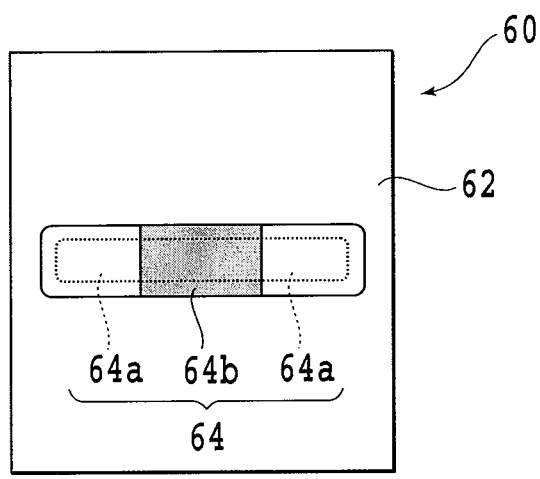
FIG. 7A is a plan view of a flow cell of Embodiment 5 of the invention.
Figure 7B:
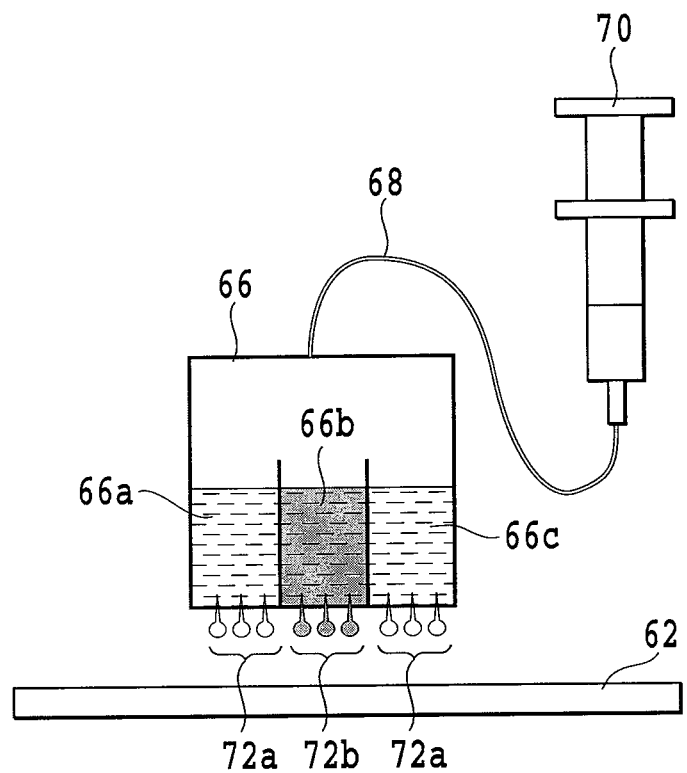
FIG. 7B is a view showing a method for manufacturing a flow cell of Embodiment 5 of the invention.

This embodiment relates to an example of a modification of the flow cell of Embodiment 1 and a method for manufacturing the same. FIG. 7A is a plan view of the subject flow cell; and FIG. 7B is a view showing an example of a method for manufacturing the subject flow cell. This is an example of providing a flow cell 60 in which a porous member 64 composed of a portion 64a where the solution used in Embodiment 1 (a porous material solution not containing an inorganic porous fine powder) is applied and a portion 64b where the solution used in Embodiment 4 (a porous material solution containing an inorganic porous fine powder) is applied onto the sample-incompatible substrate 62.

In order to obtain such a flow cell 60, as shown in FIG. 7B, for example, a container 66 is used, in which a coating solution is divided in three compartments 66a to 66c, and each of the compartments can be sealed airtight. The container 66 can be prepared by using, for example, TEFLON (a registered trademark). The container 66 has a plurality of fine openings on a bottom face 74 thereof so as to stipple an appropriate channel shape. Also, the container 66 is connected to a pressure unit such as a syringe 70, etc. via a tube 68, and respective solutions 72a and 72b are applied onto the sample-incompatible substrate 62 by an air pressure from the pressure unit (syringe 70).

Figure 7C:
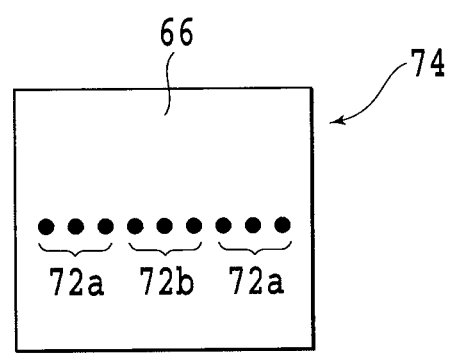
FIG. 7C is a bottom view of a container to be used for a method for manufacturing a flow cell of Embodiment 5 of the invention.

FIG. 7C is a view showing the bottom face 74 of the container 66 for carrying out application of the respective solutions 72a and 72b. By carrying out such application, the porous member 64 locally having the elements 64a and 64b having a different transfer rate from each other can be favorably formed by using the different solutions 72a and 72b. This is because the respective elements 64a and 64b of the porous member 64 as desired can be formed by simultaneous coating and drying.

Example 6

The present inventors actually prepared the flow cell 60 as shown in FIG. 7A and examined a transfer rate of a trace solution sample. The porous member 64 having a length of 1 cm and a width of 1 mm was formed on the sample-incompatible substrate 62. In this porous member 64, a ⅓ region of each of the both ends in the longitudinal direction was a portion which did not contain an inorganic porous fine powder, with a central region thereof containing an inorganic porous fine powder. In such a flow cell 60, 5 μL of a solution containing a dye (Red No. 102 (manufactured by Kyoritsu Foods Co., Inc.) was dropped on one end of the porous member 64. Though the solution sample remained as a droplet at the beginning, it thereafter penetrated into the porous member 64, and after 2.5 minutes, it reached an end of the opposite side.

In this dropping procedure, leakage of the solution sample from the side face of the porous member 64 to the sample-incompatible substrate 62 was not observed until the droplet reached the opposite side, and a sample transfer rate thereof was 4 mm/min. Though this transfer rate was a higher value as compared with the case of the flow cell as shown in Example 1 (Embodiment 1), it was a lower value as compared with the case of the flow cell as shown in Example 5 (Embodiment 4). This was caused by the fact that an inorganic fine power with high water absorbability was partially contained in the central region of the porous member 64. Accordingly, it has become clear from Embodiments 1, 4 and 5 that when a portion where an inorganic fine powder with high water absorbability is contained in a part of the porous member is interposed, and the length in the longitudinal direction thereof is properly changed, it is possible to regulate a sample movement time (namely, the sample transfer rate) from one end to the other end of the porous member.

Embodiment 6

Figure 8:
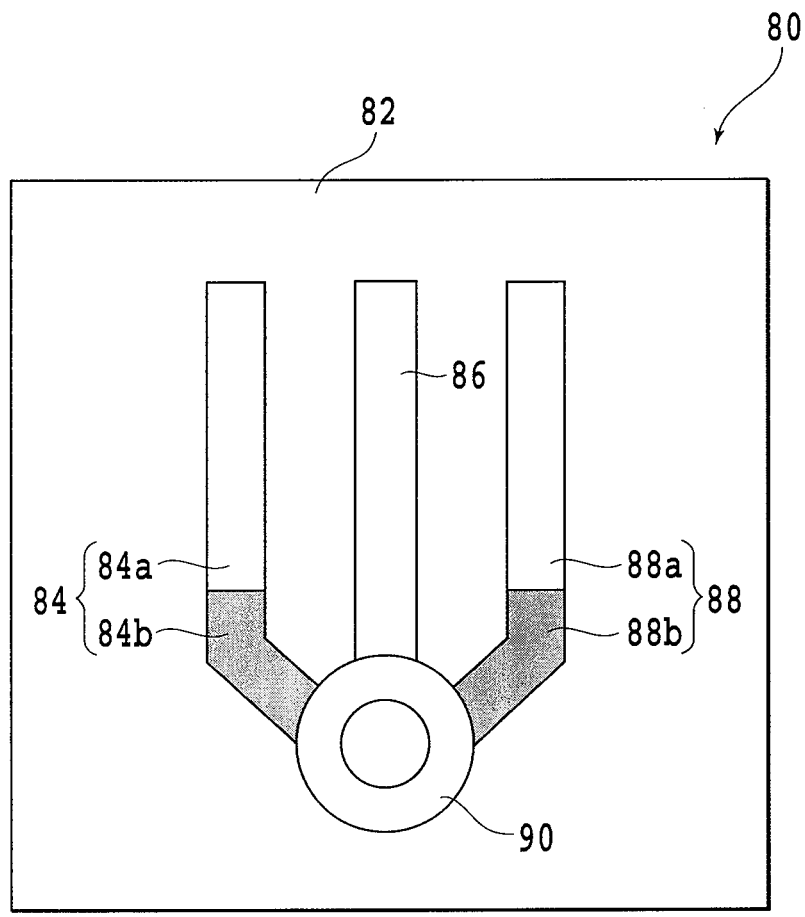
FIG. 8 is a plan view showing a flow cell of Embodiment 6 of the invention.

FIG. 8 is a plan view showing an example of a modification of the flow cell of Embodiment 1. This is an example of a flow cell to be used for carrying out a plurality of measurements or tests at the same time by using the same solution sample. That is, a flow cell 80 as shown in FIG. 8 has a structure in which three porous members 84, 86 and 88 are formed on a sample-incompatible substrate 82, and a circular sample reservoir 90 communicated with these members 84, 86 and 88 is further formed.

In the flow cell 80 of this type, after feeding a sample into the reservoir 90, the sample simultaneously penetrates into one end of each of the porous members 84, 86 and 88. In this example, since it is desired to carry out the three measurements or tests at the same time, it is desirable that the samples which have penetrated into the respective porous members 84, 86 and 88 simultaneously reach the respective other ends.

In the example as shown in FIG. 8, the porous member 86 formed in the center and the porous members 84 and 88 formed on both sides thereof have a different length from each other. Therefore, in order to make all of the arrival times of the sample at the other end identical with each other, the relatively long porous members 84 and 88 are formed with portions 84a and 88a which do not contain an inorganic porous fine powder with high water absorbing ability and portions 84b and 88b which contain the above-described powder, respectively. The sample transfer rate is regulated to increase in the portions 84b and 88b as compared with that in the other portions 84a, 86 and 88a.

Embodiment 7

Figure 9A:
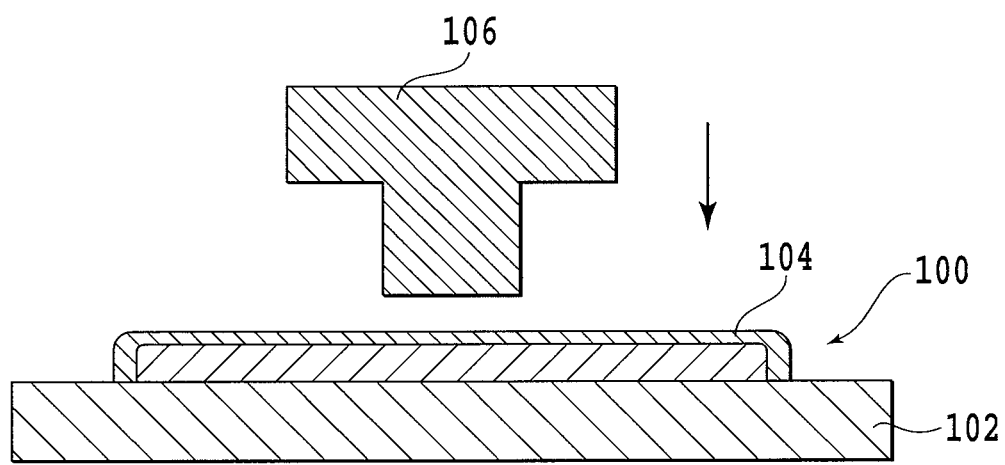
FIG. 9A is a view showing an example of a method for manufacturing a flow cell of Embodiment 7 of the invention.
Figure 9B:
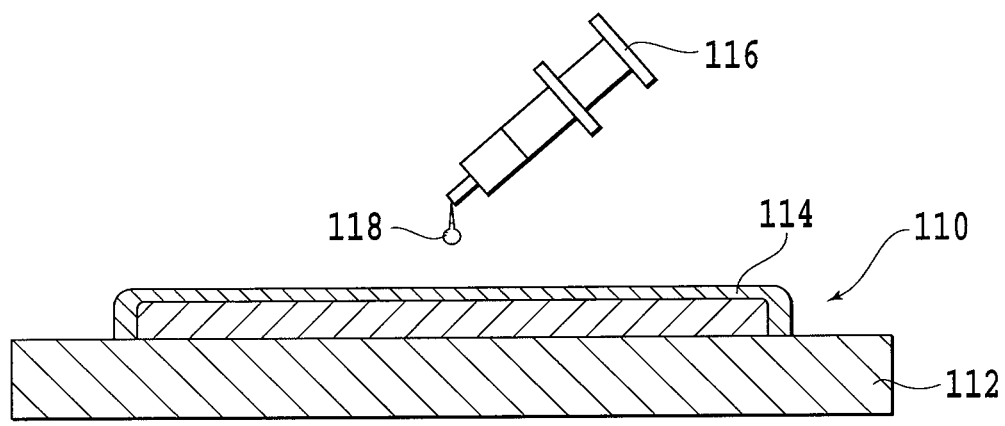
FIG. 9B is a view showing an example of a method for manufacturing a flow cell of Embodiment 7 of the invention.

This embodiment relates to a manufacturing method of a modification in which the flow cell formed in Embodiment 1 is further processed in an additional step to control the pore density or wettability of at least a part of the porous member, so that the sample transfer rate is regulated. FIG. 9A shows a modification which uses pressure applied by a die; FIG. 9B shows a modification which applies a sealing material; and FIG. 9C shows a modification which is exposed to a solvent vapor.

The example of post-processing of the flow cell as shown in FIG. 9A is an example in which a pressure is applied to a porous member 104 by a die 106 from an upper part of a flow cell 100 in which the porous member 104 is formed on a sample-incompatible substrate 102 according to the method of FIG. 10, and a network structure at a given position is compressed by the pressure. As a result, the sample transfer rate is regulated. In this way, in a region of the porous member 104 compressed by the die 106, a liquid channel of the porous member is decreased in size due to the compression, and therefore, the water absorbing ability is decreased. Therefore, the post-processing as shown in FIG. 9A is advantageous to be employed when decreasing the transfer rate.

The post-processing of the flow cell as shown in FIG. 9B is an example in which a sealing material 118 is applied by a dispenser (for example, a syringe 116, etc.) from an upper part of a flow cell 110 in which a porous member 114 is formed on a sample-incompatible substrate 112 according to the method of FIG. 10. As a result, the sample transfer rate is regulated. Here, it is preferable to use, as the sealing material 118, a material capable of being easily changed from a liquid phase to a solid phase, such as paraffins, ultraviolet light-curable resins, etc. As a result, in a region of the porous member 114 in which the sealing material 118 is applied and dried, two effects are achieved; an effect for inhibiting evaporation of the sample and an effect for narrowing the channel. Therefore, in the post-processed flow cell as shown in FIG. 9B, an effect is provided to accomplish the measurement over a long period of time, since the evaporation of the solvent does not substantially occur even when the transfer rate is reduced.

Figure 9C:
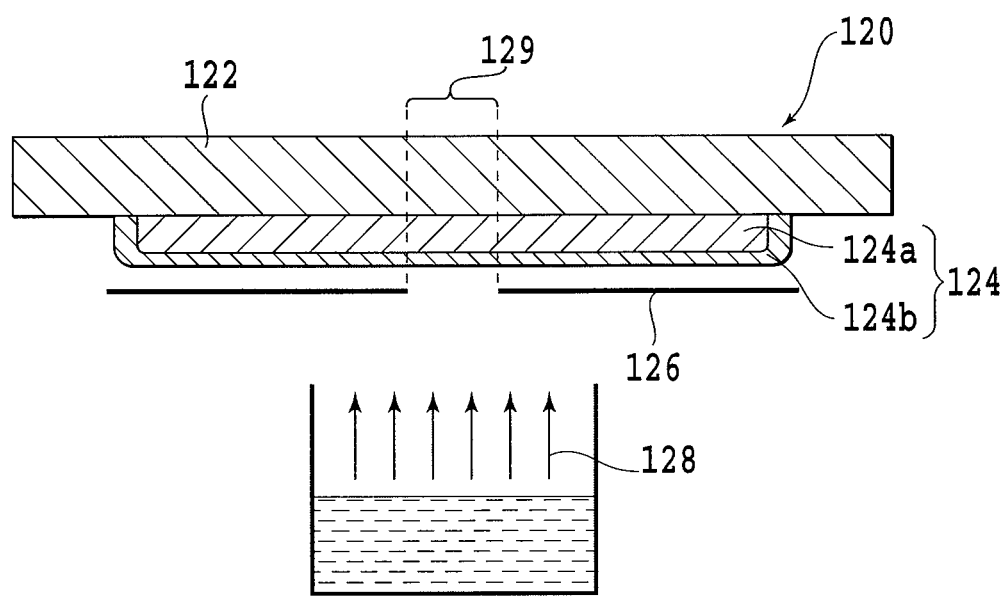
FIG. 9C is a view showing an example of a method for manufacturing a flow cell of Embodiment 7 of the invention.

The flow cell as shown in FIG. 9C is an example in which a solvent vapor 128, for example, acetone, etc., is exposed from an opposing side (a lower part in the same drawing) to a porous member 124 of a flow cell 120 in which the porous member 124 is formed on a sample-incompatible substrate 122 according to the method of FIG. 10. As a result, the sample transfer rate is regulated. Here, a region 129 of the porous member 124 to be exposed to the solvent vapor 128 can be delimited by disposing, for example, a shadow mask 126 between the vapor source and the porous member. In the region 129 to be exposed to the solvent vapor 128, a pore density is small in an air contact region 124b which is positioned outside an air non-contact region 124a and which has a smaller pore density than the subject region 124a. This is because the material in the air contact region 124b of the region 129 is dissolved in the solvent vapor and reconstituted. Accordingly, the evaporation of the sample in the region 129 is inhibited, and the water absorbing ability of the porous member 124 is decreased. Therefore, the post-processing as shown in FIG. 9C is advantageous to be employed when the transfer rate is to be decreased.

As a separate method of post-processing, there is an example in which a prescribed place of the flow cell to be formed according to FIG. 1 receives a solution droplet containing a surfactant, is infiltrated and then dried, thereby further increasing the sample compatibility of the air non-contact region in the inside of the porous member. This example demonstrates that the wettability of at least a part of the porous member is controlled, so that the water absorbing power of the sample is enhanced, thereby increasing the transfer rate of the sample. As the surfactant, Tween 20 (manufactured by GE Healthcare Biosciences) and the like are useful. For example, a mixed solution of 0.05% of Tween 20 and 99.95%) of water is dropped onto a prescribed place of the porous member, infiltrated and then dried. Such post-processing is advantageous to be employed when further increasing the transfer rate.

Embodiment 8

Figure 10A:
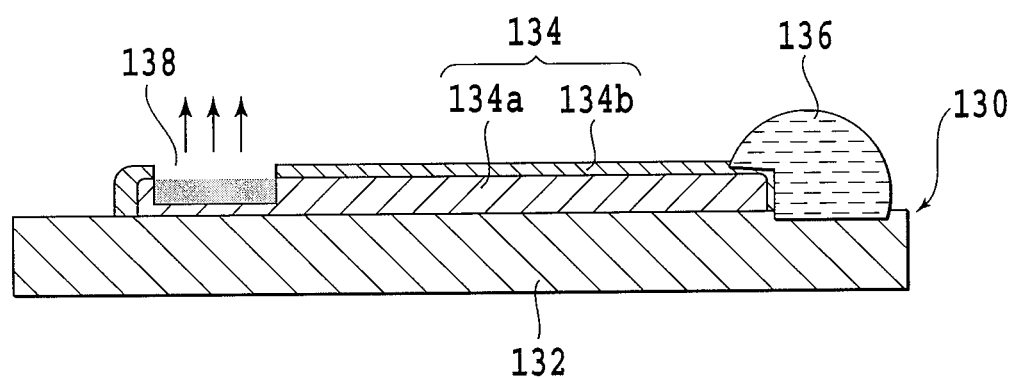
FIG. 10A is a view showing an example of a method for manufacturing a flow cell of Embodiment 8 of the invention.
Figure 10B:
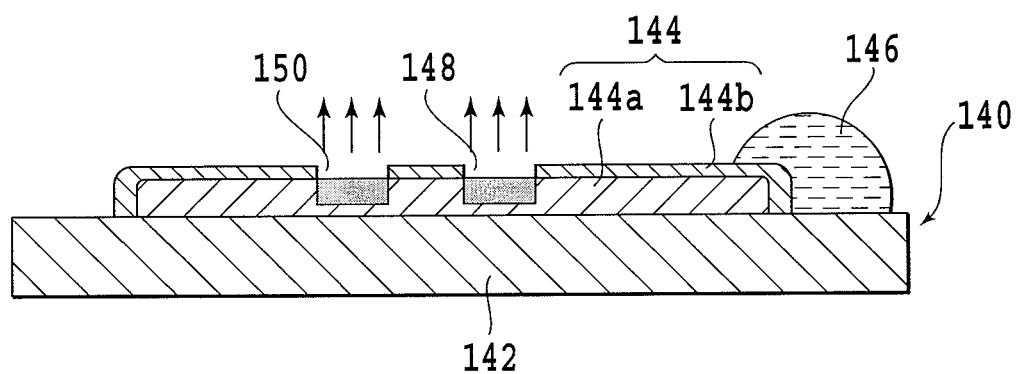
FIG. 10B is a view showing an example of a method for manufacturing a flow cell of Embodiment 8 of the invention.

FIGS. 10A and 10B are each a side view showing an example of a modification of the flow cell of Embodiment 1; FIG. 10A shows a modification by an adhesive tape; and FIG. 10B is a view showing a modification by a reactive ion etching method (hereinafter sometimes referred to as "RIE method"). All of these are an example of regulating the sample transfer rate by subjecting the flow cell to be formed by the method of Embodiment 1 to post-processing similar to Embodiment 7.

A flow cell as shown in FIG. 10A is an example of a flow cell 130 in which a porous member 134 comprises an air non-contact region 134a and an air contact region 134b is formed on a sample-incompatible substrate 132 according to the method of FIG. 1C. A part of the air contact region 134b of one end of the flow cell 130 is peeled by an adhesive tape, thereby regulating the sample transfer rate. When a dye-containing solution sample 136 was dropped on one end of the flow cell 130 of such a configuration, the sample reached a peeled portion 138 within a shorter period of time as compared with Example 1 of Embodiment 1. Also, the sample was concentrated in the peeled portion 138 by this dropping. This could be confirmed by the fact that the dye was concentrated in the peeled portion 138 due to an increase of the evaporation rate of the sample by peeling of the air contact region 134b. Therefore, the post-processing as shown in FIG. 10A is advantageous to be employed when not only the transfer rate is increased, but also a high-concentration region of the solution sample is patterned at an arbitrary position in the channel.

A flow cell 140 as shown in FIG. 10B is an example in which a porous member 144 comprises an air non-contact region 144a and an air contact region 144b is formed on a sample-incompatible substrate 142 according to the method of FIG. 1C. A part (two places in the same drawing) of the air contact region 144b of one end of the flow cell 140 is removed by an RIE method using a shadow mask, thereby regulating the sample transfer rate. When a dye-containing solution sample 146 was dropped onto one end of the flow cell 140 of such a configuration, the sample reached the removed portions 148 and 150 within a shorter period of time as compared with Example 1 of Embodiment 1. Also, the sample was concentrated in the removed portions 148 and 150 by this dropping. This could be confirmed by the fact that the dye was concentrated in the subject portions 148 and 150 due to an increase of the evaporation rate of the solvent in the removed portions 148 and 150. Therefore, the post-processing as shown in FIG. 10B is advantageous to be employed when not only the transfer rate is increased, but also a high-concentration region of the solution sample is patterned at an arbitrary position in the channel.

Embodiment 9

Figure 11A:
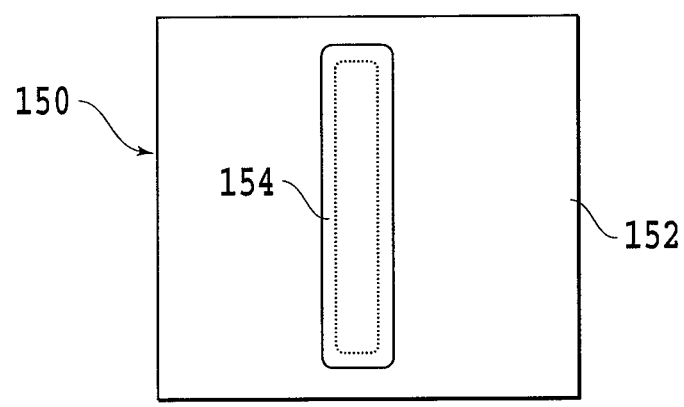
FIG. 11A is a plan view showing a flow cell before processing to be employed in a method for manufacturing a flow cell of Embodiment 9 of the invention.
Figure 11B:
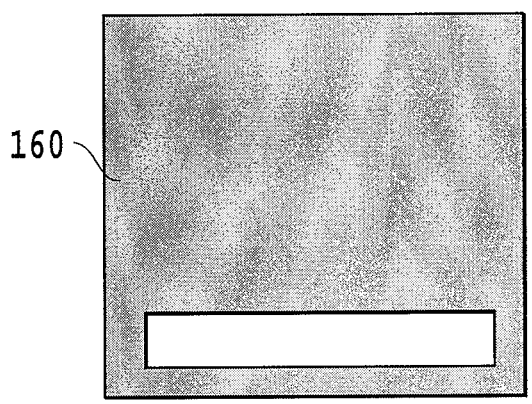
FIG. 11B is a plan view showing a shadow mask to be used in a method for manufacturing a flow cell of Embodiment 9 of the invention.
Figure 11C:
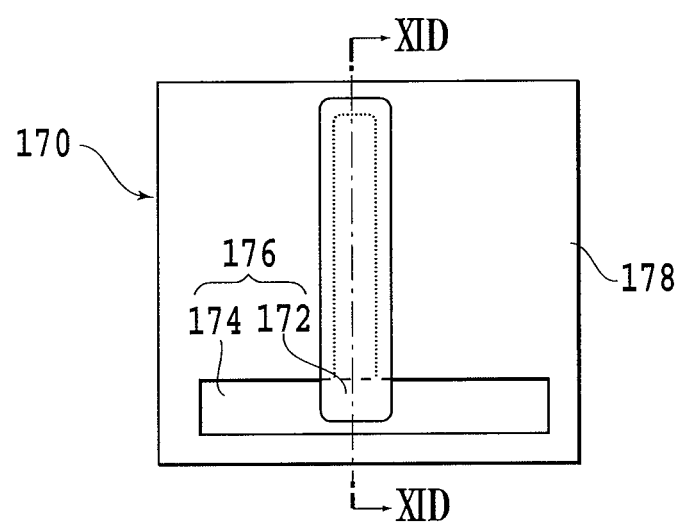
FIG. 11C is a plan view showing a flow cell to be obtained by a manufacturing method of Embodiment 9 of the invention.
Figure 11D:
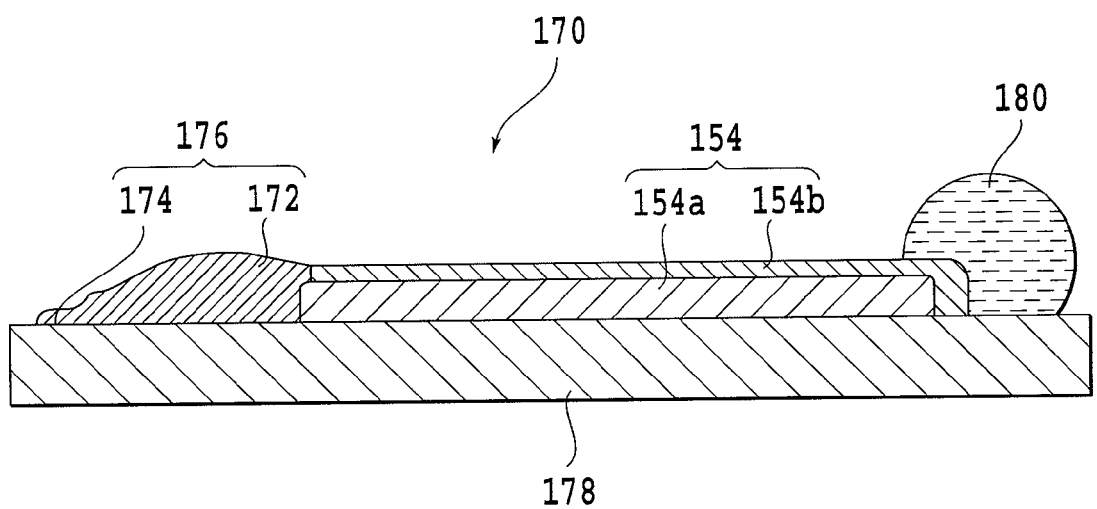
FIG. 11D is a cross-sectional view of a flow cell to be obtained by a manufacturing method of Embodiment 9 of the invention along a section line XID-XID of FIG. 11C.

FIGS. 11A to 11D are drawings showing an example of a modification of the flow cell of Embodiment 1 and a manufacturing example thereof. FIG. 11A is a plan view of a flow cell to be formed according to the method of FIG. 1C; FIG. 11B is a plan view of a shadow mask to be used for subjecting the flow cell as shown in FIG. 11A to post-processing; FIG. 11C is a plan view of a flow cell of this example after post-processing of the flow cell of FIG. 11A; and FIG. 11D is a cross-sectional view along a section line XID-XID of the flow cell as shown in FIG. 11C.

The formation method of the flow cell as shown in this embodiment is as follows. First of all, a porous member 154 is formed on a sample-incompatible substrate 152 according to Embodiment 1, thereby obtaining a flow cell 150 having the linear porous member 154 as shown in FIG. 11A. Subsequently, a shadow mask 160 as shown in FIG. 11B is disposed onto the flow cell 150, and the flow cell 150 are subjected to a plasma treatment within an RIE apparatus. By this plasma treatment, as shown in FIG. 11C, not only a porous member 172, a part of which has been peeled in the plasma treated region, is formed, but also a part 174 of the sample-incompatible substrate in the plasma treated region becomes sample-compatible. As a result, there is obtained a flow cell 170 including a sample-incompatible substrate 178 in which is formed a sample-compatible portion 176 composed of the porous member 172, a part of which has been peeled, and the part 174 of the sample-incompatible substrate having been made sample-compatible. This example demonstrates that the sample transfer rate is regulated by controlling wettability of at least a part of the sample-incompatible substrate.

As shown in FIG. 11D, in flow cell 170, the porous member 154 composed of an air non-contact region 154a and an air contact region 154b is formed on the sample-incompatible substrate 178. Here, the sample-compatible portion 176 composed from the porous member 172, a part of which has been peeled, and the part 174 of the sample-incompatible substrate is communicated with the porous member 154. When a dye-containing solution sample 180 is dropped onto one end of the flow cell 170 of such a configuration, the sample reaches the sample-compatible portion 176 in a left-hand end of the same drawing and is further spread into the sample-compatible portion 176. In this case, the flow cell 170 capable of continuously sending a liquid can be obtained, since the sample-compatible portion 176 plays the role as a drain (exhaust port).

Embodiment 10

Figure 12A:
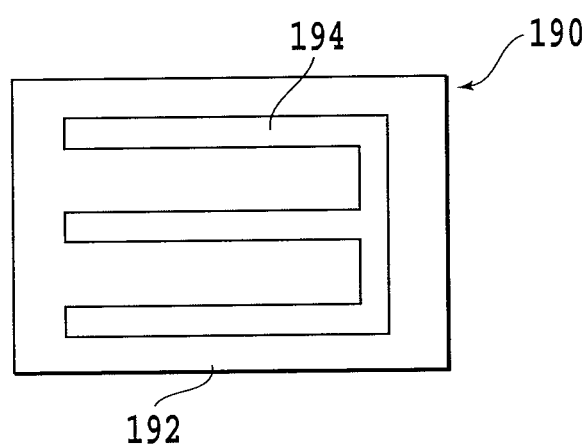
FIG. 12A is a plan view of a flow cell to be used in Embodiment 10 of the invention.
Figure 12B:
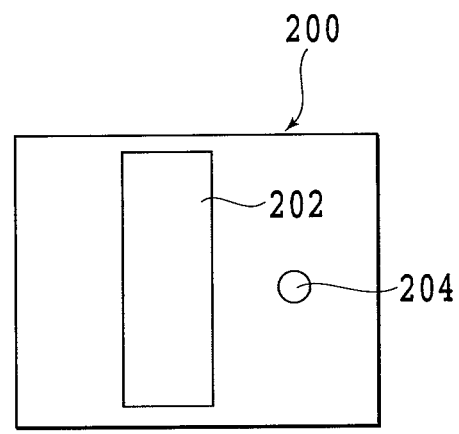
FIG. 12B is a bottom view of a second sample-incompatible substrate to be used in Embodiment 10 of the invention.
Figure 12C:
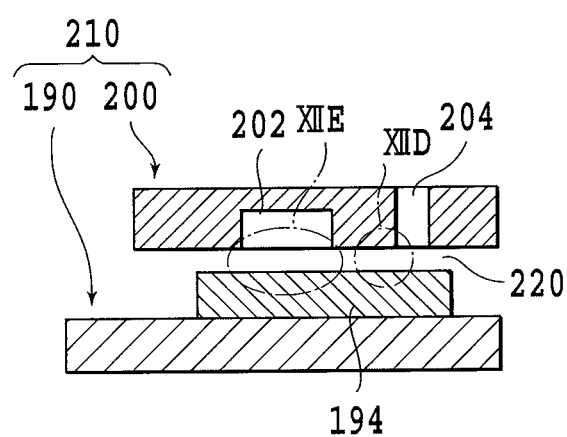
FIG. 12C is a cross-sectional view of a top cover-provided flow cell of Embodiment 10 of the invention.
Figure 12D:
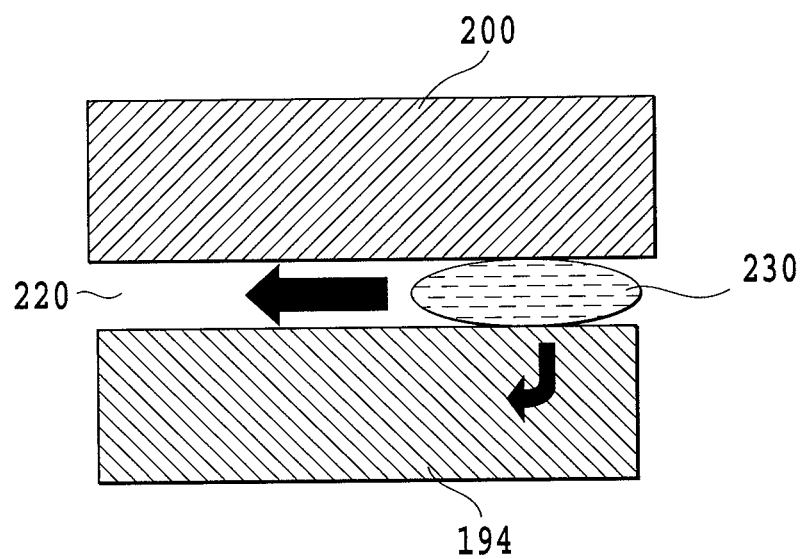
FIG. 12D is an enlarged cross-sectional view of a region XIID of FIG. 12C.
Figure 12E:
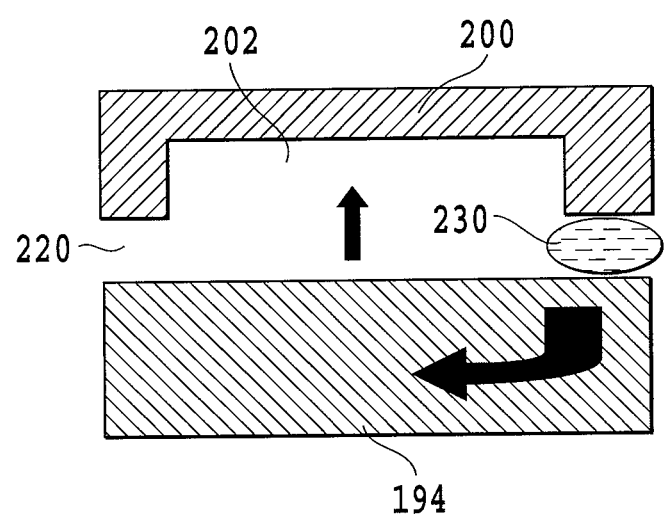
FIG. 12E is an enlarged cross-sectional view of a region XIIE of FIG. 12C.

FIGS. 12A to 12E each shows an example of a modification of a flow cell in Embodiment 7 which has been subjected to a treatment for making the cell compatible with the sample with a surfactant. FIG. 12A shows a plan view of a flow cell having been subjected to the subject sample compatibilization treatment; FIG. 12B is a bottom view of a level difference-provided sample-incompatible substrate to be used in combination with the flow cell of FIG. 12A; FIG. 12C shows a side view of a top cover-provided flow cell in which the flow cell as shown in FIG. 12A and a level difference-provided second sample-incompatible substrate as shown in FIG. 12B are disposed via a fine gap such that a level difference section 202 and a porous member 194 are opposed to each other; and FIG. 12D shows an enlarged cross-sectional view of a region XIID as shown in FIG. 12C; and FIG. 12E shows an enlarged cross-sectional view of a region XIIE as shown in FIG. 12C.

A flow cell 190 as shown in FIG. 12A is one in which the porous member 194 is formed on a sample-incompatible substrate 192, and the porous member 194 is subjected to the compatibilization treatment. Also, in a second-incompatible substrate 200 as shown in FIG. 12B, the level difference section 202 and a solution sample feed section 204 of an opened shape are formed. The second sample-incompatible substrate 200 can be prepared by using a glass substrate having been subjected to a sample incompatibility treatment, etc. This second sample-incompatible substrate 200 is a member which play a role as a top cover provided in a flow cell 210 as described below.

As shown in FIG. 12C, in the flow cell 210 provided with a top cover of this example, a fine gap 220 is formed between the flow cell 190 and the second sample-incompatible substrate 200. A width of the fine gap 220 (width in the vertical direction in the same drawing) must be made sufficiently narrow so that a capillary force can be generated. The width of the fine gap is preferably in the range of from 10 to 100 µm. The top cover-provided flow cell 210 as shown in FIG. 12C has the following advantage due to the formation of this fine gap 220 as compared with various flow cells of the foregoing Embodiments 1 to 9.

When the solution sample is fed from the solution sample feed section 204 as shown in FIG. 12C, the sample reaches the porous member 194. Then, as shown in FIG. 12D, when a part of a solution sample 230 penetrates into the porous member 194, the remainder of the solution sample 230 moves at the same time toward the left-hand side of FIG. 12D due to a capillary force working within the fine gap 220 which is defined between the porous member 194 and the second sample-incompatible substance 200. In this portion, the amount of the solution sample 230 which moves due to a capillary force is larger than the amount of the solution sample 230 which penetrates into the porous member 194.

Subsequently, as shown in FIG. 12E, when the solution sample reaches the level difference section 202 of the second sample-incompatible substrate 200, the amount of the solution sample 230 which penetrates into the porous member 194 increases as compared with the amount of the solution sample 230 which moves due to the foregoing capillary force. In addition, in this portion, the solvent in the sample evaporates in the level difference section 202, but when reaching a saturated vapor pressure, the second sample-incompatible substrate 200 plays a role as a cover. Therefore, this flow cell is advantageous for carrying out an analysis in which a change in concentration of a sample solution is small, and a relatively long period of time is required for the reaction time.

In the flow cell 210 provided with a top cover, in a region extending to the level difference section 202 corresponding to the three channels (the region as shown in FIG. 12D), the movement of the sample is achieved at a relatively high speed substantially at the same time in the three channels. On the other hand, after reaching the level difference portion 202 as shown in FIG. 12E, the sample flows at a relatively low speed in the porous member 194, since a capillary force does not work in the level difference section 202. This means that the same effect as in Embodiment 6 can be achieved by a single porous member. Since the flow cell having a top cover exhibiting the foregoing action, it is possible to achieve detection of a biological substance with high sensitivity, by using a single channel as a reference, fixing different antibodies from each other in the other two channels, respectively, and observing a difference from the reference. For example, fixing of the antibodies of a different kind in the respective channels can be carried out by spotting with a spotting device (for example, Nano-Plotter (manufactured by GeSiM, Germany), etc.).

INDUSTRIAL APPLICABILITY

The flow cell of the invention can be applied in all of the fields of handling a trace amount of chemical substance solution, such as micro-TAS, Lab-on-a-chip, micro-combinatorial chemistry, chemical IC, chemical sensor, bio sensor, microanalysis, electrochemical analysis, chromatography, QCM measurement, SPR measurement, ATR measurement, etc.

What is claimed is:

1. A flow cell for an aqueous sample, the flow cell comprising:
   a hydrophobic substrate; and
   a porous member provided on the hydrophobic substrate, the porous member comprising:
      a first region having a network structure; and
      a second region positioned on the first region and having a lower pore density than the first region;
   wherein a cavity is formed between the hydrophobic substrate and the second region, the first region being positioned in the cavity,
   wherein the first region constitutes a channel in which an aqueous sample is configured to laterally flow, and
   wherein a capillary force generated within the porous member is a drive force for pumping a liquid.

2. The flow cell according to claim 1, wherein the first region has a higher hydrophilicity than the second region.

3. The flow cell according to claim 1, wherein the porous member is formed of a cellulose.

4. The flow cell according to claim 1, wherein the porous member further contains particles.

5. The flow cell according to claim 1, wherein openings are present in at least a part of the second region.

6. The flow cell according to claim 1, wherein at least a part of the porous member communicates with a hydrophilic region formed on a surface of the hydrophobic substrate and wherein the hydrophilic region acts as a drain.

7. The flow cell according to claim 1, further comprising a second hydrophobic substrate disposed on the porous member to form a fine gap between the porous member and the second hydrophobic substrate, wherein a width of the fine gap falls within the range of from about 10 µm to about 100 µm.

8. The flow cell according to claim 7, wherein the second hydrophobic substrate includes a recess opposed to the porous member.

9. The flow cell according to claim 1, wherein the first and second regions directly contact the hydrophobic substrate.

10. The flow cell according to claim 1, wherein the second region bounds side and top portions of the cavity.

11. A flow cell for a non-aqueous sample, the flow cell comprising:
    a hydrophilic substrate; and
    a porous member positioned on the hydrophilic substrate, the porous member comprising:
       a first region having a network structure; and
       a second region positioned on the first region and having a lower pore density than the first region;

wherein a cavity is formed between the hydrophilic substrate and the second region, the first region being positioned in the cavity, wherein the first region constitutes a channel in which a non-aqueous sample is configured to laterally flow, and wherein a capillary force generated within the porous member is a drive force for pumping a liquid.

12. The flow cell according to claim 11, wherein the porous member is formed of a cellulose.

13. The flow cell according to claim 11, wherein the porous member further contains particles.

14. The flow cell according to claim 11, wherein openings are present in at least a part of the second region.

\* \* \* \* \*